(12) United States Patent
Zhu et al.

(10) Patent No.: US 8,435,962 B2
(45) Date of Patent: May 7, 2013

(54) TRIACETYL-3-HYDROXYPHENYLADENOSINE AND ITS USE FOR REGULATING BLOOD FAT

(75) Inventors: Haibo Zhu, Beijing (CN); Song Wu, Beijing (CN); Linghua Hao, Beijing (CN); Kai Qu, Beijing (CN); Ping Zhu, Beijing (CN); Xing Wang, Beijing (CN); Wei Li, Beijing (CN)

(73) Assignee: Institute of Mataria Medica, Chinese Academy of Medical Sciences, Beijing (CN)

( * ) Notice: Subject to any disclaimer, the term of this patent is extended or adjusted under 35 U.S.C. 154(b) by 0 days.

(21) Appl. No.: 13/255,153

(22) PCT Filed: Mar. 10, 2009

(86) PCT No.: PCT/CN2009/070725
§ 371 (c)(1),
(2), (4) Date: Nov. 18, 2011

(87) PCT Pub. No.: WO2010/040286
PCT Pub. Date: Apr. 15, 2010

(65) Prior Publication Data
US 2012/0053143 A1    Mar. 1, 2012

(51) Int. Cl.
*A01N 43/04* (2006.01)
*A61K 31/70* (2006.01)
*C07H 19/20* (2006.01)

(52) U.S. Cl.
USPC .......................................... 514/46; 536/26.13

(58) Field of Classification Search .................. None
See application file for complete search history.

(56) References Cited

U.S. PATENT DOCUMENTS
2006/0276428 A1    12/2006 Elzein et al.
2007/0087994 A1    4/2007 Elzein et al.

FOREIGN PATENT DOCUMENTS
CN    1616459 A    5/2005

OTHER PUBLICATIONS

Kwatra et al., Journal of Medicinal Chemistry, 1987, vol. 30, No. 5, pp. 954-956.*

Beukers, M.W. et al., "N6-Cyclopentyl-2-(3-phenylaminocarbonyltriazene-1-yl)adenosine (TCPA), a Very Selective Agonist with High Affinity for the Human Adenosine A1 Receptor" Journal of Medicinal Chemistry (2003) pp. 1492-1503, vol. 46, No. 8.
Matsuda, A. et al., "Mutagenicity of (p-nitrophenyl)adenines in *Salmonella typhimurium*" Mutation Research (1991) pp. 93-100, vol. 263, No. 2.
International Search Report dated Jul. 16, 2009 issued in corresponding International Application No. PCT/CN2009/070725.

* cited by examiner

*Primary Examiner* — Traviss C McIntosh, III
(74) *Attorney, Agent, or Firm* — Scully, Scott, Murphy & Presser, P.C.

(57) ABSTRACT

The invention discloses triacetyl-3-hydroxyphenyladenosine represented by formula (I), the preparation, the pharmaceutical composition and the use thereof. Specially, the invention discloses a new compound of 2',3',5'-tri-O-acetyl-$N^6$-(3-hydroxyphenyl)adenosine. Using hypoxanthine nucleoside as starting material, the compound is prepared by acetylating with acetic anhydride, chlorinating with thionyl chloride, and being substituted with 3-hydroxy aniline. The invention also discloses the pharmaceutical composition comprising triacetyl-3-hydroxyphenyladenosine. The dosage forms of the said pharmaceutical composition include tablet, capsule, pill, injection, sustained release preparation, controlled release preparation or particulate delivery system. The medicament for treatment or precaution of hyperlipemia prepared by the compound of the invention has the advantages of significant hypolipidemic activity, less toxicity and adverse effect as well as slow metabolism in vivo.

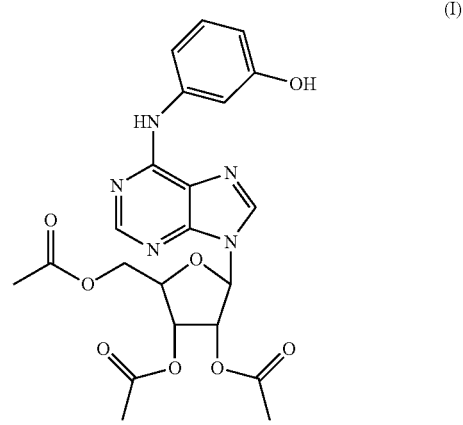

10 Claims, No Drawings

TRIACETYL-3-HYDROXYPHENYLADENOSINE AND ITS USE FOR REGULATING BLOOD FAT

FIELD OF THE INVENTION

The present invention relates to Tri-acetyl-3-hydroxylphenyl adenosine, the preparation method thereof, the pharmaceutical compositions containing them, and their use in the manufacture of pharmaceutical for hyperlipidemia, belongs to the field of medical technology.

BACKGROUND OF THE INVENTION

Basic researches and clinical trial results have proved that hyperlipidemia, including hypercholesteremia, hypertriglyceridemia, and complex hyperlipidemia, is key risk factor of stroke, cornary heart disease, myocardial infarction, and sudden death due to heart failure. Moreover, hyperlipidemia is a key risk factor to promote hypertension, impaired glucose tolerance (IGT) and diabetes. It also leads to adiposis hepatica, liver cirrhosis, pancreatitis, subhyaloid hemorrhage, acroisa, peripheral angiopathy, and hyperuricacidemia.

At present, the clinically widely used lipid regulating agents contain cholesterol biosynthetic enzyme inhibitor statins and peroxisome proliferative activated receptor (PPARs) transcription factor activator fibrates. Statins decrease endogenous synthesis of cholesterol and reduce low density lipoprotein cholesterol (LDL-C) via inhibition on activity of HMG-CoA reductase. Meanwhile, statins reduce blood content of LDL by increasing or activating the express level of LDL receptor on hepatocellular surface. Fibrates are a class of lipid regulator that mainly acting on triglyceride. The two classes of drugs are main trend of lipid regulators. The clinic pharmacodynamic action is exact, the potent dosage is low, and the bioavailability is high. However, side effect of the two classes, such as liver injury and rhabdomyolysis, causes security problems being worried and worth concerned.

Compared to the drug development pattern in western drug manufacturers, finding new type lipid regulator in Chinese traditional herbal medicine is a new drug developing way that suitable for our country. Lots of Chinese herbal medicine with good lipid regulating action and low adverse effect has wide application perspective. For instance, triterpenes in Chinese hawthorn inhibit cholesterol synthesis in vivo and accelerate cholesterol clearance. Anthraquinone is the active components contained by rhubarb, semen, and fleeceflower root, it promotes enterokinesia, and increase cholesterol excretion. The lipid lowering effect of Alisma L. orientate Juzep is associated to interference of triterpene compounds with endogenous metabolism of cholesterol. Danshensu in salvia miltiorrhiza indicates inhibitory action on cholesterol synthesis in vitro. Salvia miltiorrhiza increases excretion of bile acid. Gypenosides in Gold Theragran can reduce the level of blood LDL-C, total cholesterol, and triglyceride, and elevate the level of HDL-C.

DISCLOSURE OF THE INVENTION

In one aspect, the present invention relates to a new adenosine compound $O^{2'},O^{3'},O^{5'}$-tri-acetyl-$N^6$-(3-hydroxylphenyl)adenosine.

In another aspect, the present invention also relates to a process of preparation compound $O^{2'},O^{3'},O^{5'}$-tri-acetyl-$N^6$-(3-hydroxylphenyl)adenosine.

In yet another aspect, the present invention also relates to a pharmaceutical composition comprising compound $O^{2'},O^{3'},O^{5'}$-tri-acetyl-$N^6$-(3-hydroxylphenyl) adenosine.

In yet another aspect, the present invention also relates to the use of compound $O^{2'},O^{3'},O^{5'}$-tri-acetyl-$N^6$-(3-hydroxylphenyl)adenosine for the manufacture of a medicament for prevention or treatment of hyperlipidemia.

The scheme described below was used to solution in the present invention:

The structure of $O^{2'},O^{3'},O^{5'}$-tri-acetyl-$N^6$-(3-hydroxylphenyl)adenosine are described as Formula (I).

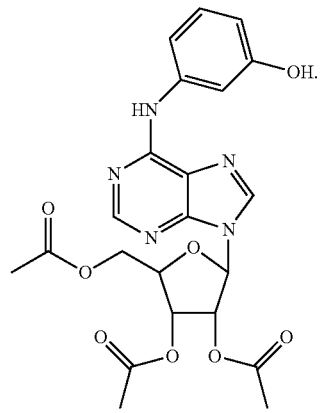

(I)

The present invention relates to a process for preparing compound (I) are described below:

Step 1: Acetic anhydride was added to a suspension of inosine in organic solvent gave the product $O^{2'},O^{3'},O^{5'}$-tri-acetylinosine.

Step 2: The product from step1, namely $O^{2'},O^{3'},O^{5'}$-tri-acetylinosine can be converted to $O^{2'},O^{3'},O^{5'}$-tri-acetyl-6-chloroadenosine by carrying out the teaction with $SOCl_2$.

Step 3: $O^{2'},O^{3'},O^{5'}$-tri-acetyl-6-chloroadenosine was dissolved in an organic solvent and upon reaction with 3-aminophenol gave the product compound $O^{2'},O^{3'},O^{5'}$-tri-acetyl-$N^6$-(3-hydroxylphenyl)adenosine.

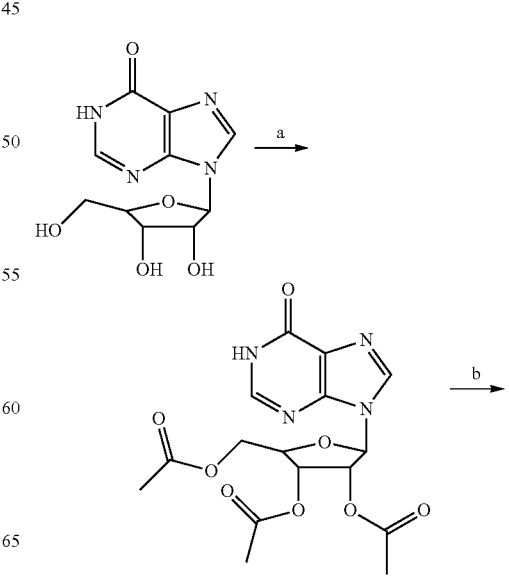

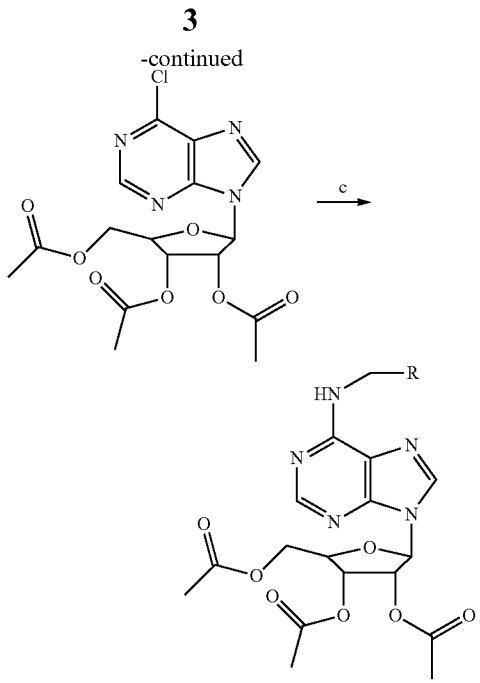

whersas, R is 3-hydroxylphenyl

Step one: the organic solvent selected from pyridine; the acetic anhydride was added at −5 to 5° C., then stirred at 20 to 30° C.

Step two: the reaction was carried one in the presence of triethylamine.

Step three: the final product is purified by chromatographed, eluent is ethyl acetate:petroleumether=2:1.

The present invention also relates to a pharmaceutical composition comprising a compound of $O^{2'},O^{3'},O^{5'}$-tri-acetyl-$N^6$-(3-hydroxylphenyl)adenosine as active ingredient. The pharmaceutical composition can be prepared according to methods well known in the art. The compound of the present invention can be formulated into any dosage forms suitable for administration to human or animals in combination with one or more pharmaceutically acceptable solid or liquid excipients and/or adjuvants. In general, the content of the compound of the present invention in the pharmaceutical composition is from 0.1 to 95% by weight.

The compound according to the present invention or a pharmaceutical composition comprising the compound can be administered in unit dose form, the routes of administration may be intestinal or parenteral, such as oral, intravenous, intramuscularly, subcutaneous, nasal, mouth mucosa, ophthalmic, pulmonary and respiratory tract, dermal, vaginal, rectal administration etc.

The dosage forms for administration may be liquid, solid or semisolid dosage forms. The liquid dosage forms may be solutions (including true solutions and colloid solutions), emulsions (including o/w type, w/o type and multiple emulsions), suspensions, injections (including aqueous injections, powder injections and infusions), eye drops, nasal drops, lotions and liniments etc.; the solid dosage forms may be tablets (including conventional tablets, enteric tablets, buccal tablets, dispersible tablets, chewable tablets, effervescent tablets, orally disintegrating tablets), capsules (including hard capsules, soft capsules, enteric capsules), granules, granules, pellets, dropping pills, suppositories, membranes, patches, aerosols/powder inhalations, sprays, etc.; the semisolid dosage forms may be ointments, gels, pastes, etc.

The compounds of present invention can be formulated into common formulations, as well as sustained release formulations, controlled release formulations, targeting formulations and various particulate delivery systems.

To formulate the compounds of present invention into tablets, a variety of excipients well known in the art can be widely used, including diluents, binders, wetting agents, disintegrants, lubricants, glidants. The diluents may be starches, dextrins, sucrose, glucose, lactose, mannitol, sorbitol, xylitol, microcrystalline cellulose, calcium sulfate, calcium hydrogen phosphate, calcium carbonate and the like; the wetting agents may be water, ethanol, isopropanol and the like; the binders may be starch slurry, dextrins, syrup, honey, glucose solution, microcrystalline cellulose, acacia mucilage, gelatin slurry, sodium carboxymethylcellulose, methylcellulose, hydroxypropylmethylcellulose, ethyl cellulose, acrylic resins, carbomer, polyvinylpyrrolidones, polyethylene glycols and the like; the disintegrants may be drying starches, microcrystalline cellulose, low substituted hydroxypropylcellulose, cross-linked polyvinylpyrrolidones, croscarmellose sodium, sodium carboxymethyl starch, sodium bicarbonate and citric acid, polyoxyethylene sorbitol fatty acid esters, sodium lauryl sulfate and the like; the lubricants and glidants may be talc, silicon dioxide, stearate, tartaric acid, liquid paraffin, polyethylene glycols and the like.

The tablets may be further processed to form coated tablets, e.g. sugar-coated tablets, film-coated tablets, enteric-coated tablets, or double-layer tablets and multi-layer tablets.

In order to formulate the dosing unit into capsules, the compounds according to the present invention as active ingredient can be mixed with diluents and glidants, and the mixtures are then loaded directly in hard or soft capsules. The compounds according to the present invention as active ingredient can also firstly be formulated, together with diluents, binders and disintegrants, into granules or pellets, then they are loaded in hard or soft capsules. The diluents, binders, wetting agents, disintegrants, glidants for preparing the tablets of the compounds according to the present invention can also be used for preparing the capsules of the compounds according to the present invention.

To formulate the compounds according to the present invention into injections, water, ethanol, isopropanol, propylene glycol or a mixture thereof can be used as solvent, and to which suitable amount of solubilizers, cosolvents, pH modifiers, osmotic pressure controlling agents can be added. The solubilizers or auxiliary solvents may be poloxamer, lecithin, hydroxypropyl-β-cyclodextrin, and the like; the pH modifiers may be phosphates, acetates, hydrochloric acid, sodium hydroxide, and the like; the osmotic pressure controlling agents may be sodium chloride, mannitol, glucose, phosphate, acetate, and the like. For the preparation of lyophilized powder injections, mannitol, glucose, etc. can also be added as support agents.

In addition, the colorants, preservatives, fragrant agents, flavoring agents or other additives may also be added to the pharmaceutical formulations if necessary. the pharmaceutical formulations also contains other lipid regulating agents.

In yet another aspect, the invention discloses the use of 2',3',5'-tri-O-acetyl-N6-(3-hydroxyphenyl)adenosine for the preparation of drugs for the treatment or prophylaxis of hyperlipidemia. It has the advantages of significant hypolipidemic activity, less toxicity and adverse effect as well as slow metabolism in vivo.

In order to achieve the purpose of treatment and enhance the effect of treatment, the medicament of the present invention or pharmaceutical composition can be administrated by any known manner for administration.

The dose of the compounds or pharmaceutical compositions of the present invention will vary in a wide range depending on the nature and severity of the diseases to be prevented or treated, individual condition of the patients or animals, administration routes, dosage forms, and the like. In general, the suitable daily dose range of the compounds according to the present invention is from 0.001 to 150 mg/Kg body weight, preferably from 0.1 to 100 mg/Kg body weight, more preferably from 1 to 60 mg/Kg body weight, most preferably from 2 to 30 mg/Kg body weight. Said dose may be administered as a single dose unit or divided dose units, depending on the clinical experience of the physicians and the dose regimen including the use of other therapeutic manners.

The compounds or compositions of the present invention may be administered alone or in combination with other therapeutic agents or the agents for symptomatic treatment. When a compound of the present invention is synergistic with other therapeutic agents, its dose should be adjusted according to the practical condition.

EXAMPLES

The following Examples illustrate the invention, but it is not intended that the invention be limited to the example. $^1$H-NMR in all case are consistent with the structure. Characteristic chemical shift (δ) expressed with (shift from TMS for a particular proton in Hz)/(spectrometer frequency in MHz) and the main peak named with abbreviations: for example, s, single peak; d, double peak; t, triple peak; q, quartet peak; m, multiple peak; br, broad peak; dd, double-double peak. Mass spectrometry (m/z) records by ESI. Using the following abbreviation for solvent in common use: DMSO, Deuterium dimethyl sulfone.

Example 1

Synthesis of $O^{2'},O^{3'},O^{5'}$-tri-acetyl-$N^6$-(3-hydroxylphenyl)adenosine (ws070117)

Step 1: Acetic anhydride (16 mL) was added to a suspension of inosine (5.36 g) in dry pyridine (25 mL) at 0° C. and stirred at room temperature for 6 h. The solvent was evaporated in vacuo. Water 75 mL was added to the residue, the suspension was stirred for ½ h then filtered and washed with water (2×50 mL) yielding the pure white product $O^{2'},O^{3},O^{5'}$-tri-acetylinosine.

Step 2: $O^{2'},O^{3},O^{5'}$-tri-acetylinosine was dissolved in dry $CH_2Cl_2$ (50 mL) and dry DMF (1 ml) and heated to 40° C. A solution of $SOCl_2$ (3.3 g) in $CH_2Cl_2$ (2.5 mL) was added dropwised. The reaction mixture was gently refluxed for an additional 6 h. The reaction mixture was cooled to room temperature and diluted with $CH_2Cl_2$. The organic layer was washed with saturated $NaHCO_3$ solution (2×50 mL) and brine (2×50 mL) and (dried anhydrous sodium sulfate). The organic phase was concentrated in vacuo and used for the subsequent reaction without any further purification.

Step 3: To a solution of $O^{2'},O^{3'},O^{5'}$-tri-acetyl-6-chloroadenosine (5.4 g) in absolute ethanol (30 mL) were added 3-aminophenol (4.28 g) and dry triethylamine (3.96 g), and the mixture was refluxed 8 h at 60° C. The solution was allowed to cool and was concentrated in vacuo and the residue was chromatographed (ethyl acetate:petroleumether=2:1) to give $O^{2'},O^{3'},O^{5'}$-tri-acetyl-$N^6$-(3-hydroxylphenyl)adenosine as a white solid (1.51 g).

$^1$H-NMR (400 MHz, DMSO) δ: 9.83 (s, 1H); 9.32 (s, 1H); 8.52 (s, 1H); 8.41 (s, 1H); 7.48 (t, 1H); 7.30 (d, 1H); 7.08 (t, 1H); 6.45 (dd, 1H); 6.26 (d, 1H); 6.05 (t, 1H); 5.64 (t, 1H); 4.42 (q, 1H); 4.37 (q, 1H); 4.25 (q, 1H); 2.11 (s, 3H); 2.04 (s, 1H); 2.00 (s, 3H).

ESI: m/z [MH$^+$] 486.3753

Pharmacological Experiment

Example 2

Effect of Ws070117 on Plasma Lipid in Hyperlipidemia Rat

Methods:

2.1 Animal Modeling and Grouping

After a week of accommodation, except control group (20 rat), all the rats (120 rats) were fed with high-fat laboratory chow. 4 weeks later, according to the serum cholesterol (TC) and triglyceride (TG) level, animals were divided into six groups: Simvastatin group (2 mg/kg); Fenofibrate (50 mg/kg); WS070117 (12 mg/kg); WS070117 (6 mg/kg); WS070117 (3 mg/kg), 20 rats each group.

2.2 Drug Treatment

After four weeks high-fat diet modeling, rats were treated with different drugs by intragastric administration. Control animals received an equal volume of vehicle.

2.3 Plasma Parameter Analysis

At the end of 4 weeks drug treatment, animals were fasted for 12 hours before anesthetizing by intraperitoneal injection of pentobarbitale sodium (45 mg/kg), and anticoagulated by 100 U/kg heparin through caudal vein injection. Blood samples were collected from the abdominal aorta within 15 min, and serum was separated. Serum TC, TG, HDL-C, LDL-C, ALT, FFA were detected. Liver and the fat pad behind the belly were separated and weighed, the liver and retroperitoneal fat were weighed too. Liver SOD and MDA were detected by kit after homogenized. The left rats (10 rats each group) drug treatment was withdrawn while high-fat diet modeling continued. Two weeks later, blood sample was collected from the orbit, and serum TC, TG were detected.

Results 1: Effects of WS070117 on Plasma Lipid in Hyperlipidemia Rats

After high-fat diet feeding, blood TC, TG, LDL-C and FFA were increased, HDL-C/LDL-C was decreased, the rats experienced hyperlipidemia. After WS070117 treatment, blood TC, TG and LDL-C were decreased, HDL-C/LDL-C was increased. WS070117 had a regulation effect on blood lipid level, and WS070117 6 mg/kg had a significant effect on rats FFA. (Table 1)

TABLE 1

Effects of WS070117 on plasma lipid in hyperlipidemia rats

| Groups | Dose mg/kg | n | TC mmol/L | TG mmol/L | HDL-C mmol/L | LDL-C mmol/L | HDL/LDL | FFA mmol/L |
|---|---|---|---|---|---|---|---|---|
| Control | — | 10 | 1.69 ± 0.23 | 0.60 ± 0.20 | 0.52 ± 0.09 | 0.89 ± 0.12 | 0.58 ± 0.13 | 0.88 ± 0.23 |
| Modle | — | 10 | 2.78 ± 0.44### | 1.37 ± 0.74## | 0.51 ± 0.10 | 1.46 ± 0.20### | 0.35 ± 0.08### | 1.24 ± 0.33# |

TABLE 1-continued

Effects of WS070117 on plasma lipid in hyperlipidemia rats

| Groups | Dose mg/kg | n | TC mmol/L | TG mmol/L | HDL-C mmol/L | LDL-C mmol/L | HDL/LDL | FFA mmol/L |
|---|---|---|---|---|---|---|---|---|
| Simvastatin | 2 | 10 | 2.22 ± 0.36** | 0.76 ± 0.21* | 0.59 ± 0.13 | 1.24 ± 0.24* | 0.50 ± 0.16* | 0.96 ± 0.39 |
| Fenofibrate | 50 | 10 | 2.23 ± 0.53* | 0.70 ± 0.19* | 0.59 ± 0.17 | 1.16 ± 0.28* | 0.53 ± 0.16** | 1.13 ± 0.30 |
| WS070117 | 12 | 10 | 2.30 ± 0.29** | 0.55 ± 0.19** | 0.56 ± 0.10 | 1.24 ± 0.20* | 0.47 ± 0.13* | 0.97 ± 0.27 |
| WS070117 | 6 | 10 | 2.11 ± 0.24*** | 0.52 ± 0.13** | 0.59 ± 0.18 | 1.19 ± 0.18** | 0.52 ± 0.19* | 0.94 ± 0.17* |
| WS070117 | 3 | 10 | 2.39 ± 0.34* | 0.67 ± 0.15** | 0.58 ± 0.10 | 1.38 ± 0.27 | 0.43 ± 0.12 | 1.04 ± 0.24 |

$p < 0.05$,
$p < 0.01$,
$p < 0.001$ vs control group;
*$p < 0.05$.
**$p < 0.01$,
***$p < 0.001$ vs model group Result 2: Effects on the Weight of Hyperlipidemia Rats' Retroperitoneal Fat The results showed that the weight of rats' retroperitoneal fat significantly increased by continually feeding high-fat chow while it obviously decreased after administration of WS070117, which indicated that WS070117 might significantly inhibit the accumulation of retroperitoneal fat (Table 2).

TABLE 2

Effects on the retroperitoneal fat weight of hyperlipidemic rats treated by WS070117

| | Dose | | Rats |
|---|---|---|---|
| Groups | mg/kg | n | Fat weight (g/100 g body weight) |
| Normal | — | 10 | 0.64 ± 0.24* |
| Model | — | 10 | 0.98 ± 0.31# |
| Simvastatin | 2 | 10 | 0.70 ± 0.28 |
| Fenofibrate | 50 | 10 | 0.68 ± 0.16* |
| WS070117 | 12 | 10 | 0.64 ± 0.22* |
| WS070117 | 6 | 10 | 0.67 ± 0.12** |
| WS070117 | 3 | 10 | 0.67 ± 0.33* |

$p < 0.05$,
$p < 0.01$,
$p < 0.001$ vs control group;
*$p < 0.05$.
**$p < 0.01$,
***$p < 0.001$ vs model group Result 3: Effects on Hepatic SOD Activity and MDA Content of Hyperlipidemia Rats The results showed that the hepatic MDA content of the rats significantly increased while the SOD activity significantly decreased after their having high-fat diets for 4 weeks. The hepatic SOD activity significantly increased after administration with simvastatin, fenofibrate and WS070117. WS070117 was indicated to have an anti-oxidant effect for the fact that it decreased hepatic MDA content (Table 3).

TABLE 3

Effects of therapeutic treatment of WS070117 on the hepatic SOD activity and MDA content of hyperlipidemia rats

| | Dose | Rats | |
|---|---|---|---|
| Groups | mg/kg | SOD U/g pr | MDA mmol/g pr |
| Normal | — | 128.8 ± 36.3 | 5.99 ± 2.91 |
| Model | — | 77.7 ± 19.2### | 10.91 ± 2.05### |
| Simvastatin | 2 | 99.5 ± 20.2* | 9.29 ± 2.73 |
| Fenofibrate | 50 | 103.6 ± 27.9* | 9.35 ± 2.40 |
| VS070117 | 12 | 107.7 ± 26.4** | 8.29 ± 2.78* |
| WS070117 | 6 | 102.0 ± 24.4* | 8.71 ± 2.83 |
| WS070117 | 3 | 93.3 ± 37.5 | 8.51 ± 3.32 |

$p < 0.05$,
$p < 0.01$,
$p < 0.001$ vs control group;
*$p < 0.05$,
**$p < 0.01$,
***$p < 0.001$ vs model group Result 4: Effects on the Liver Weight and Serum ALT Activity of Hyperlipidemia Rats The results indicated that the serum ALT activity tended to increase but without statistic significance compared with normal groups after the rats were continually given high-fat diet. The liver index (the liver weight/100 g body weight) significantly increased (Table 4).

TABLE 4

Effects of WS070117 on liver weight and the serum ALT activity of hyperlipidemia rats

| Groups | Dose mg/kg | Liver weight (g/100 g body weight) Rats | ALT (U/L) Rats |
|---|---|---|---|
| Normal | — | 3.18 ± 0.31 | 35.3 ± 14.4 |
| Model | — | 3.97 ± 1.10# | 45.2 ± 18.4 |
| Simvastatin | 2 | 3.96 ± 0.93 | 40.4 ± 15.6 |
| Fenofibrate | 50 | 4.08 ± 0.36 | 40.3 ± 18.0 |
| WS070117 | 12 | 3.26 ± 0.54 | 42.0 ± 16.6 |
| WS070117 | 6 | 3.21 ± 0.38 | 41.6 ± 19.8 |
| WS070117 | 3 | 3.22 ± 0.48 | 42.9 ± 13.7 |

$p < 0.05$,
$p < 0.01$,
$p < 0.001$ vs control group;
*$p < 0.05$,
**$p < 0.01$,
***$p < 0.001$ vs model group Result 5: Changes of Blood Lipid Level in Hyperlipidemia Rats after WS070117 Withdrawal for 2 Weeks The results showed that the serum TC content was significantly lower than that of the model group after withdrawal from drugs for 2 weeks, which indicated that WS070117 could sustain its blood-fat regulatory effect for more than 2 weeks (Table 5).

TABLE 5

Effects of WS070117 on the serum lipid of experimental hyperlipidemia rats after withdrawal from drugs

| Groups | Dose mg/kg | n | Rats TC mmol/L | TG mmol/L |
| --- | --- | --- | --- | --- |
| Normal | — | 8 | 1.85 ± 0.41 | 0.71 ± 0.23 |
| Model | — | 8 | 2.48 ± 0.33## | 1.20 ± 0.29### |
| Simvastatin | 2 | 8 | 2.14 ± 0.33* | 0.94 ± 0.24* |
| Fenofibrate | 50 | 8 | 2.08 ± 0.49* | 1.03 ± 0.19 |
| VS070117 | 12 | 8 | 2.15 ± 0.32* | 1.01 ± 0.38 |
| WS070117 | 6 | 8 | 2.02 ± 0.43* | 1.03 ± 0.22 |
| WS070117 | 3 | 8 | 2.12 ± 0.45 | 1.04 ± 0.19 |

$p < 0.05$,
$p < 0.01$,
$p < 0.001$ vs control group;
*$p < 0.05$,
**$p < 0.01$,
***$p < 0.001$ vs model group Example 3

Effects of WS070117 on Plasma Lipid Regulation in Hyperlipidemia Hamster

Methods:

3.1 Animal Modeling and Grouping

After a week of accommodation, except control group (n=12) all the hamsters (n=72) were fed with high-fat laboratory chow. 4 weeks later, according to the serum cholesterol (TC) and triglyceride (TG) level, animals were divided into six groups: model group; Simvastatin group (2 mg/kg); Fenofibrate (50 mg/kg); WS070117 (12 mg/kg); WS070117 (6 mg/kg); WS070117 (3 mg/kg), 12 hamsters each group.

3.2 Drug Treatment

After four weeks high-fat diet modeling, rats were treated with different drugs by intragastric administration. Control animals received an equal volume of vehicle.

3.3 Plasma Parameter Analysis

At the end of 4 weeks drug treatment, animals were fasted for 12 hours (10 of each group). The next day, they were anesthetized by intraperitoneal injection of pentobarbitale sodium (45 mg/kg). Blood samples were collected from the abdominal aorta within 15 min, and plasma was separated. Plasma TC, TG, HDL-C, LDL-C, ALT, FFA were detected. Liver and the retroperitoneal fat were separated and weighed, the liver and fat index were calculated. Liver SOD and MDA were detected by kit after homogenized. The left hamsters (10 each group) drug treatment was withdrawn while high-fat diet modeling continued. Two weeks later, blood sample was collected from the orbit and serum TC and TG were detected.

Results 1: Effects of WS070117 on Plasma Lipid in Hyperlipidemia Hamsters

After high-fat diet feeding, blood TC, TG, LDL-C and FFA were increased, but the rate of HDL-C/LDL-C was decreased. After WS070117 treatment, blood TC, TG and LDL-C were decreased, the rate HDL-C/LDL-C was increased. WS070117 had a regulation effect on blood lipid level. (Table 6)

TABLE 6

Effects of WS070117 on plasma lipid in hyperlipidemia hamsters

| Groups | Dose mg/kg | n | TC mmol/L | TG mmol/L | HDL-C mmol/L | LDL-C mmol/L | HDL/LDL |
| --- | --- | --- | --- | --- | --- | --- | --- |
| Control | — | 10 | 2.40 ± 0.76 | 1.77 ± 0.44 | 0.76 ± 0.17 | 1.60 ± 1.14 | 0.59 ± 0.24 |
| Model | — | 10 | 7.05 ± 2.89### | 5.23 ± 1.36### | 1.24 ± 0.21## | 5.03 ± 2.70## | 0.30 ± 0.17## |
| Simvastatin | 2 | 10 | 4.46 ± 1.63* | 3.20 ± 1.70** | 1.12 ± 0.21 | 2.57 ± 0.53* | 0.45 ± 0.12* |
| Fenofibrate | 50 | 10 | 4.76 ± 1.58* | 3.80 ± 1.04* | 1.48 ± 0.40 | 3.04 ± 0.82* | 0.50 ± 0.13** |
| WS070117 | 12 | 10 | 3.60 ± 1.84** | 3.44 ± 1.29** | 1.24 ± 0.40 | 2.26 ± 0.47** | 0.59 ± 0.31* |
| WS070117 | 6 | 10 | 4.19 ± 1.14** | 3.67 ± 1.46* | 1.14 ± 0.18 | 3.00 ± 0.90* | 0.40 ± 0.09* |
| WS070117 | 3 | 10 | 4.35 ± 0.93* | 4.26 ± 1.52 | 1.24 ± 0.26 | 3.68 ± 1.44 | 0.37 ± 0.11 |

$p < 0.05$,
$p < 0.01$,
$p < 0.001$ vs control group;
*$p < 0.05$.
**$p < 0.01$,
***$p < 0.001$ vs model group Result 2: Effects of WS070117 on Retroperitoneal Fat Hyperlipidemia Hamsters After high-fat diet feeding, retroperitoneal fat were increase. After WS070117 treatment, retroperitoneal fat were decreased. (table 7)

TABLE 7

Effect of WS070117 on retroperitoneal fat hyperlipidemia hamsters

| Group | Dose mg/kg | n | retroperitoneal fat(g/100g) |
|---|---|---|---|
| Control | — | 10 | 0.87 ± 0.25*** |
| Model | — | 10 | 1.61 ± 0.30### |
| Simvastatin | 2 | 10 | 0.97 ± 0.19*** |
| Fenofibrate | 50 | 10 | 1.07 ± 0.16*** |
| WS070117 | 12 | 10 | 1.31 ± 0.27* |
| WS070117 | 6 | 10 | 1.23 ± 0.23** |
| WS070117 | 3 | 10 | 1.26 ± 0.34* | p < 0.05,
p < 0.01,
p < 0.001 vs control group;
*p < 0.05,
**p < 0.01,
***p < 0.001 vs model group Result 3: Antioxidation Action of WS070117 in Hyperlipidemic Hamsters As shown in Table 8, compared with the control group, hamsters fed with high fat diet manifested a higher level of MDA, and the activity of SOD was significantly lower. However, MDA concentration of the hamsters treated with simvastatin, fenofibrate or WS070117 was lower than the model group, which indicated that WS070117 possesses anti-oxidative effect.

TABLE 8

Effects of WS070117 on hepatic SOD activity and MDA concentration in Hyperlipidemic hamsters' livers

| group | dose mg/kg | SOD U/g pr | MDA mmol/g pr |
|---|---|---|---|
| control | — | 132.0 ± 44.4 | 4.99 ± 1.86 |
| model | — | 74.6 ± 30.0## | 8.50 ± 2.65## |
| Simvastatin | 2 | 94.6 ± 38.0 | 4.48 ± 0.96*** |
| Fenofibrate | 50 | 94.0 ± 16.3 | 5.94 ± 1.05* |
| VS070117 | 12 | 91.9 ± 22.9 | 4.60 ± 0.92*** |
| WS070117 | 6 | 95.1 ± 31.6 | 4.23 ± 0.72*** |
| WS070117 | 3 | 84.0 ± 19.6 | 4.80 ± 1.20*** | p < 0.05,
p < 0.01,
p < 0.001 vs control group;
*p < 0.05,
**p < 0.01,
***p < 0.001 vs model group Result 4 Effects of WS070117 on Liver Weight and ALT Activity in Hyperlipidemic Animals As shown in Table 9, serum ALT activity of hamsters fed with high fat diet or administered with lipid emulsion increased slightly, but showing no significance. In model group, rat liver index was higher (p<0.05). And serum ALT activity slightly reduced in hyperlipidemic rats administrated of WS070117.

TABLE 9

Effects of WS070117 on liver weight and ALT activity in Hyperlipidemic hamsters

| group | dose mg/kg | Liver weight (g/100 g body weight) rat | ALT (U/L) hamster |
|---|---|---|---|
| control | — | 3.18 ± 0.31 | 81.9 ± 19.9 |
| model | — | 3.97 ± 1.10# | 110.9 ± 43.1 |
| Simvastatin | 2 | 3.96 ± 0.93 | 99.9 ± 23.5 |
| Fenofibrate | 50 | 4.08 ± 0.36 | 97.3 ± 37.8 |
| WS070117 | 12 | 3.26 ± 0.54 | 95.2 ± 34.8 |
| WS070117 | 6 | 3.21 ± 0.38 | 91.7 ± 23.1 |
| WS070117 | 3 | 3.22 ± 0.48 | 100.7 ± 38.2 | p < 0.05,
p < 0.01,
p < 0.001 vs control group;
*p < 0.05,
**p < 0.01,
***p < 0.001 vs model group Result 5 Hypolipidemic Effect of WS070117 Lasted for 2 Weeks at Least after Drug Discontinuance.

As shown in Table 10, serum lipid levels of hamsters treated with WS070117 at 12 mg/kg and 6 mg/kg were significantly lower than those of the model group, which indicated that the hypolipidemic effect of WS070117 lasted for 2 weeks at least after drug discontinuance.

TABLE 10

Effects of WS070117 on serum lipid level in Hyperlipidemic hamsters after drug discontinuance

| group | dose mg/kg | TC mmol/L | TG mmol/L |
|---|---|---|---|
| control | — | 2.47 ± 0.99 | 1.80 ± 0.41 |
| model | — | 6.73 ± 1.84### | 5.45 ± 1.46### |
| Simvastatin | 2 | 4.91 ± 1.18* | 4.58 ± 1.01 |
| Fenofibrate | 50 | 5.29 ± 2.13 | 4.16 ± 0.86* |
| WS070117 | 12 | 4.61 ± 1.11* | 3.82 ± 0.66* |
| WS070117 | 6 | 5.02 ± 1.35* | 4.16 ± 0.77* |
| WS070117 | 3 | 5.34 ± 1.32 | 4.36 ± 1.27 | p < 0.05,
p < 0.01,
p < 0.001 vs control group;
*p < 0.05,
**p < 0.01,
***p < 0.001 vs model group In conclusion, pharmadynamics studies demonstrated that O2',O3',O5'-tri-acetyl-N6-(3-hydroxylphenyl)adenosine (WS070117), a novel synthesized compound, could regulate lipid levels of hyperlipidemic model animals such as hamsters and rats, indicating that O2',O3',O5'-tri-acetyl-N6-(3-hydroxylphenyl)adenosine played a therapeutic role in the experimental hyperlipemia.

The invention claimed is:

1. $O^{2'},O^{3'},O^{5'}$-tri-acetyl-N6-(3-hydroxylphenyl) adenosine represented by the following general formula (I)

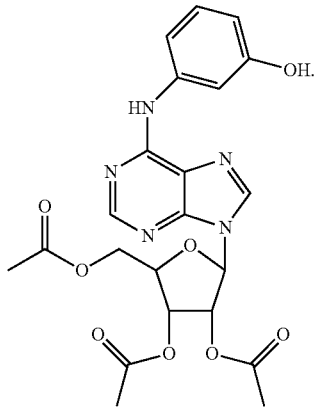
(I)

2. A process for preparing $O^{2'},O^{3'},O^{5'}$-tri-acetyl-$N^{6}$-(3-hydroxylphenyl) adenosine represented by the following general formula (I)

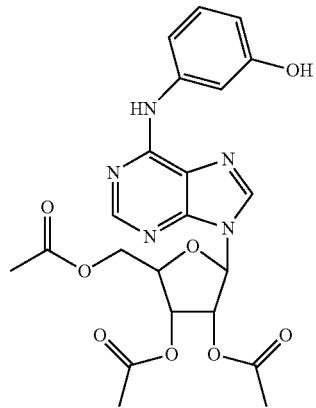
(I)

comprising:
Step 1: adding acetic anhydride to a suspension of inosine in organic solvent to produce $O^{2'},O^{3'},O^{5'}$-tri-acetylinosine;
Step 2: $O^{2'},O^{3'},O^{5'}$-tri-acetylinosine with $SOCl_2$ to produce $O^{2'},O^{3'},O^{5'}$-tri-acetyl-6chloroadenosine; and
Step 3: dissolving $O^{2'},O^{3'},O^{5'}$-tri-acetyl-6-chloroadenosine in an organic solvent and reacting with 3-aminophenol to produce the compound $O^{2'},O^{3'},O^{5'}$-tri-acetyl-$N^{6}$-(3-hydroxylphenyl) adenosine, and purifying the compound.

3. The process of claim 2, wherein the organic solvent is pyridine in Step 1.

4. The process of claim 2, wherein in Step 1 the acetic anhydride is added at −5 to 5° C., then stirred at 20 to 30° C.

5. The process of claim 2, wherein in Step 2 the reaction is carried out in the presence of triethylamine.

6. The process of claim 2, wherein in Step 3 the final product is purified by chromatography using eluent which comprises ethyl acetate and petroleum ether at a ratio of 2:1.

7. A pharmaceutical composition comprising a pharmaceutically effective dosage of $O^{2'},O^{3'},O^{5'}$-tri-acetyl-N6-(3-hydroxylphenyl) adenosine represented by the following general formula (I), and a pharmaceutically acceptable carrier

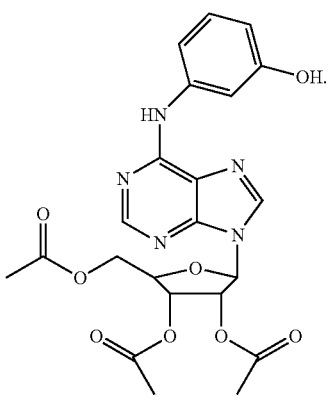
(I)

8. The pharmaceutical composition according to claim 7 comprising at least one other hypolipidemic drug.

9. The pharmaceutical composition according to claim 7 or 8, wherein said the pharmaceutical composition is formulated as tablets, capsules, pills, injections, sustained-release formulations, controlled-release formulations, targeted preparations, or fine particle delivery systems.

10. A method of treating hyperlipidemia in a subject, comprising administering to the subject $O^{2'},O^{3'},O^{5'}$-tri-acetyl-N6-(3-hydroxylphenyl)adenosine represented by the following general formula (I)

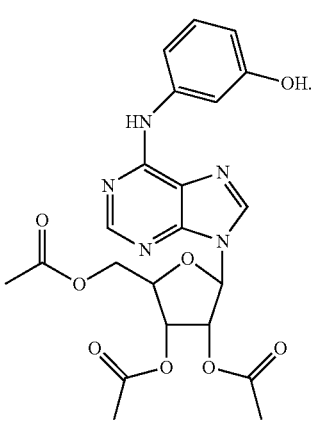
(I)

* * * * *

UNITED STATES PATENT AND TRADEMARK OFFICE
CERTIFICATE OF CORRECTION

PATENT NO. : 8,435,962 B2
APPLICATION NO. : 13/255153
DATED : May 7, 2013
INVENTOR(S) : Haibo Zhu et al.

It is certified that error appears in the above-identified patent and that said Letters Patent is hereby corrected as shown below:

In the Claims

Column 13, line 50, Claim 2, should read: Step 2: <u>reacting</u> $O^{2'}$, $O^{3'}$, $O^{5'}$-tri-acetylinosine with $SOCl_2$ to produce Signed and Sealed this
Tenth Day of September, 2013

Teresa Stanek Rea
*Acting Director of the United States Patent and Trademark Office*